(12) United States Patent
Mahadevan et al.

(10) Patent No.: US 8,835,145 B2
(45) Date of Patent: Sep. 16, 2014

(54) THROMBOLYTIC ENZYME AND A PROCESS FOR ITS PREPARATION

(75) Inventors: Perurmadom Ramaiyer Mahadevan, Andhra Pradesh (IN); Sita Mahadevan, legal representative, Andhra Pradesh (IN); Subrahamanyam Chivukula Sekar, Clayton (AU); Sundaramurthy Suresh Babu, Chennai (IN)

(73) Assignees: National Research Development Corporation, New Delhi (IN); India and Malladi Drugs Pharmaceuticals Ltd., Chennai (IN)

(*) Notice: Subject to any disclaimer, the term of this patent is extended or adjusted under 35 U.S.C. 154(b) by 1090 days.

(21) Appl. No.: 11/907,512

(22) Filed: Oct. 12, 2007

(65) Prior Publication Data
US 2009/0285793 A1 Nov. 19, 2009

Related U.S. Application Data

(62) Division of application No. 10/849,229, filed on May 20, 2004, now Pat. No. 7,776,574.

(51) Int. Cl.
*A61K 38/43* (2006.01)
*C12N 1/20* (2006.01)
*C12N 9/00* (2006.01)
*C12N 9/54* (2006.01)
*C12N 9/74* (2006.01)
*C12Q 1/56* (2006.01)
*C12N 9/64* (2006.01)

(52) U.S. Cl.
CPC ....... *C12N 9/6432* (2013.01); *C12Y 304/21006* (2013.01); *Y10S 435/814* (2013.01); *Y10S 435/832* (2013.01)
USPC ............ 435/183; 424/94.1; 435/13; 435/214; 435/221; 435/252.5; 435/814; 435/832

(58) Field of Classification Search
None
See application file for complete search history.

(56) References Cited

U.S. PATENT DOCUMENTS

| 4,009,264 A | 2/1977 | Mizutani |
| 5,434,059 A | 7/1995 | Balaraman et al. |
| 5,700,669 A | 12/1997 | Hanson et al. |
| 2005/0260704 A1 | 11/2005 | Mahadevan et al. |

*Primary Examiner* — Debbie K Ware
(74) *Attorney, Agent, or Firm* — Venable LLP; Keith G. Haddaway; Annette K. Kwok

(57) ABSTRACT

The invention relates to a thrombolytic enzyme referred to as Thrombinase having a molecular weight of 31,000 to 32,000. Such a thrombolytic enzyme can be used for dissolving blood clots. The process comprises culturing a filtrate of *Bacillus sphaericus* sero type H5a 5b, removing the cell, subjecting the cell supernatant to filtration, salting out the retentate, subjecting the precipitate to dialysis, reprecipitating the precipitate and then reconstituting in buffer and finally decolorizing, purifying and dialyzing.

12 Claims, 6 Drawing Sheets

Fluorescence Spectrum Of Thrombinase

Excitation wavelength 280nm

Buffer - Citrate-Phosphate (50mM)

US 8,835,145 B2

THROMBOLYTIC ENZYME AND A PROCESS FOR ITS PREPARATION

CROSS-REFERENCE TO RELATED APPLICATION

This application is a divisional and claims priority to U.S. patent application Ser. No. 10/849,229, filed May 20, 2004, now U.S. Pat. No. 7,776,574, issued on Aug. 17, 2010, the entire contents of which are incorporated herein by reference.

FIELD OF INVENTION

This invention relates to novel thrombolytic enzyme. The thrombolytic enzyme of the present invention is named as Thrombinase having a molecular weight in the range of 31,000 to 32000 Daltons. The novel enzyme is prepared in high purity and is useful for dissolving blood clots. The enzyme of the present invention dissolves the blood clot much faster than the currently available thrombolytic agents like Streptokinase, Urokinase.

The invention also relates to a process for the preparation of the novel Thrombinase, which is a thrombolytic enzyme at higher yields and better purity levels having a molecular weight in the range of 31000 to 32000 Daltons.

BACKGROUND OF INVENTION

Thrombinase is an enzyme which dissolves the blood clot much faster than the currently available thrombolytic agents like Streptokinase, Urokinase, Tissue Plasminogen Activator and hence has advantages for the treatment of cerebral thrombosis, myocardial infarction, deep vein thrombosis and in the prevention of post surgical adhesion.

U.S. Pat. No. 5,434,059 dated Jul. 18, 1995 describes a process for the preparation of a thrombolytic enzyme, namely Thrombinase with the improvement of yield by modification of the fermentation medium and increase in the purity by modification of the downstream processing methods. Such a thrombolytic enzyme has a molecular weight of 18,500. The Indian Application No. 2671/DEL/98 relates to the process for the preparation of Thrombinase.

OBJECTS OF THE INVENTION

The main objective of the present invention is to provide a novel thrombolytic enzyme named as Thrombinase having a molecular weight in the range of 31000 to 32000 Daltons, which is useful for dissolving blood clots.

Another objective of this invention is to provide an improved process for the preparation of the novel Thrombinase having a molecular weight in the range of 31000 to 32000 Daltons and having a higher yield in comparison to that of the known art.

Yet another object of this invention is to provide a process for the preparation of Thrombinase having a molecular weight in the range of 31000 to 32000 Daltons and having a better purity in comparison to that of the known art.

Still another object of this invention is to provide a process for the preparation of Thrombinase having a molecular weight in the range of 31000 to 32000 Daltons and having reduced volume handling.

DESCRIPTION OF INVENTION

Figure 1:
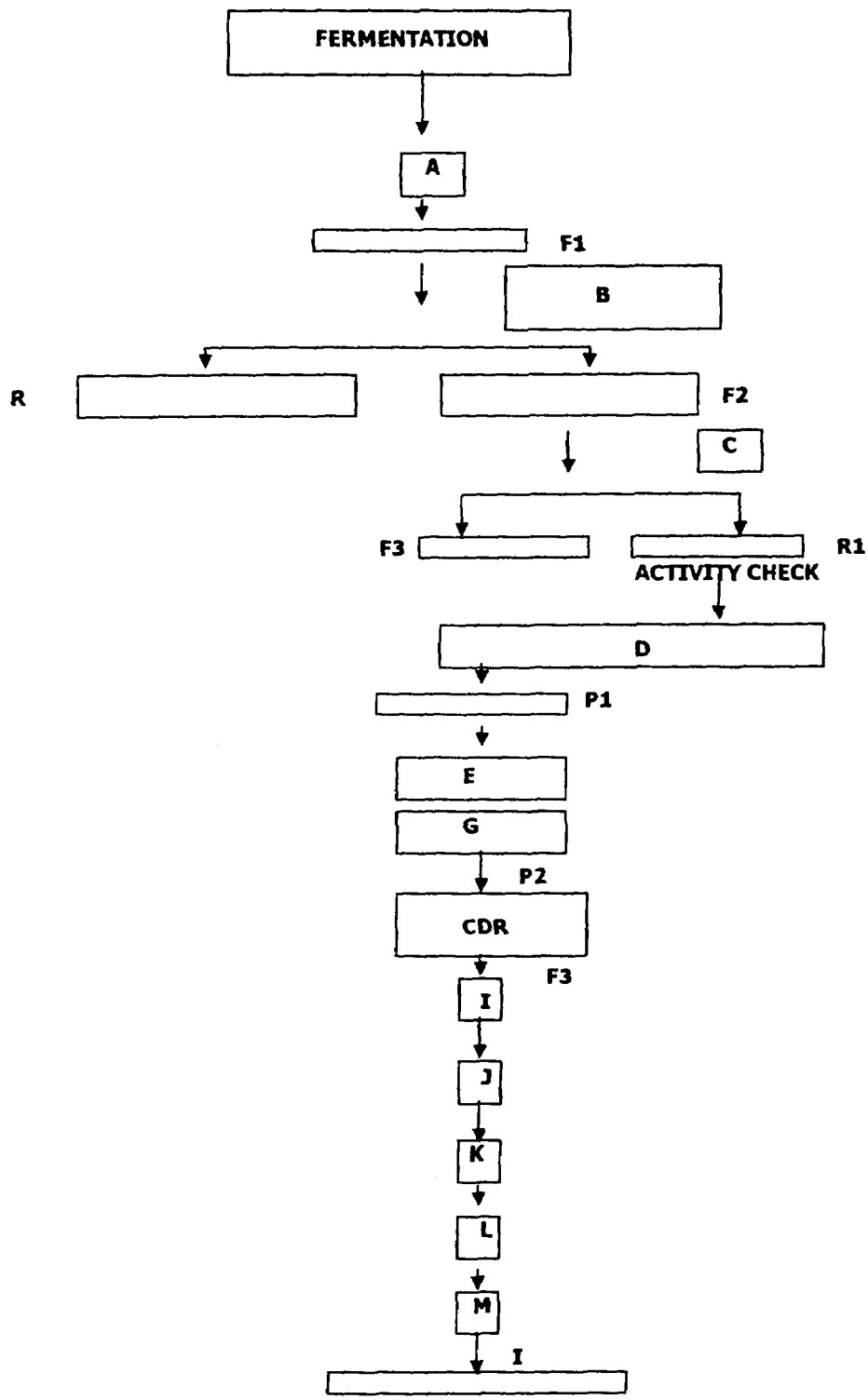
FIG. 1 is a flow diagram of the process.

Accordingly, the present invention relates to a novel thrombolytic enzyme named as Thrombinase having a molecular weight in the range of 31000 to 32000 Daltons, more preferably around 31700 and having high purity, which is useful for dissolving blood clots. According to another embodiment of the present invention there is provided a process for the preparation of thrombolytic enzyme having a molecular weight in the range of 31000 to 32000 Daltons comprising, (i) Culturing the filtrate of *Bacillus sphaericus* serotype H5a 5b having the accession no. 18949 NRRL (dated 17 Mar. 1992) deposited at Agriculture Research Service, US Department of Agriculture and Midwest Area, 1815, North University Street, Peoria, Ill., USA, in a culture medium consisting of yeast extract with one or more of constituents selected from peptone, sodium acetate, beef extract, sodium chloride, Soya peptone, and ammonium sulphate (ii) Removing the cell formed by cross flow filtration using 0.22µ filter, (iii) subjecting the cell supernatant thus obtained to two step ultra filtration using 1,00,000 MW (Molecular Weight) cut off membrane followed by ultra filtration of the filtrate thus obtained using 10,000 MW cut off membrane, (iii) salting out the retentate with ammonium sulphate, (iv) subjecting the resulting precipitate to dialysis, (v) re-precipitating the precipitate using ice-cold acetone, (vi) reconstituting in buffer, (vii) decolorizing by using modified CDR (Cell Debris Remover) treatment, dialyzing, lyophilizing, (viii) purifying firstly by ion exchange chromatography followed by gel filtration chromatography and (ix) dialyzing the fraction showing fibrinolytic activity and lyophilizing to obtain purified Thrombinase having a molecular weight in the range of 31,000 to 32000 Daltons.

The amount of the constituents present in the Culture medium employed is 0.03 to 1.5% of yeast extract, 0.2 to 1.5% peptone, 1 to 1.6% sodium acetate, 0.3 to 0.5% beef extract, 0.2 to 0.5% sodium chloride, 0.5 to 1% Soya peptone, and 0.68% ammonium sulphate In a preferred embodiment of the invention the pH of the culture medium used is in the range of 7.2 to 8.0.

In another embodiment of the invention the ammonium sulphate used is in an amount in the range of 20 to 40%.

The buffer used is Tris 0.01 M

In yet another embodiment of the invention the buffer used is Tris 0.01 M and the pH used is 8 and amount of the ice-cold acetone and crude enzyme used are in the ratio of 1:1 to 1:1.5 (v/v).

Various media along with their composition were used for the fermentation of *Bacillus sphaericus* and various yields of the new Thrombinase were obtained. Several media compositions were tried for optimization of Thrombinase yield. These include completely synthetic media, synthetic media with different percentages of yeast extract and complex media. Growth was very poor in completely synthetic medium unless it is supplemented with yeast extract. Table 1 gives a few media, which showed good results in shake flask

TABLE 1

| MEDIUM | COMPOSITION | | BATCH VOLUME | ACTIVITY IU/LIT |
|---|---|---|---|---|
| 1. SYBN | Soya peptone | 0.5% | 100 ml | $4.46 \times 10^7$ |
| | YE | 0.05% | | |
| | BE | 0.3% | | |
| | NaCl | 0.5% | | |
| 2. HNYS-II | Soya peptone | 0.5% | 100 ml | $6.9 \times 10^7$ |
| | NaCl | 0.5% | | |
| | YE | 1% | | |
| 3. NMYS-V | Soya peptone | 1% | 100 ml | $5.3 \times 10^7$ |
| | YE | 0.5% | | |
| | NaCl | 0.5% | | |
| 4. MNYS-V | Peptone | 0.5% | 100 ml | $1.15 \times 10^7$ |
| | YE | 1% | | |
| | BE | 0.3% | | |
| | NaCl | 0.3% | | |
| 5. SAMNYS-II | SA | 1% | 100 ml | $3.03 \times 10^7$ |
| | Peptone | 0.5% | | |
| | NaCl | 0.5% | | |
| | YE | 1% | | |
| 6. SAY | SA | 1.6% | 100 ml | $5.4 \times 10^7$ |
| | YE | 0.4% | | |
| | AS | 0.68% | | |
| 7. SAYP-I | SA | 1.6% | 100 ml | $1.94 \times 10^7$ |
| | Peptone | 0.40% | | |
| | AS | 0.68% | | |
| | YE | 0.4% | | |
| 8. SAYP-II | SA | 1.6% | 100 ml | $2.8 \times 10^8$ |
| | Peptone | 0.40% | | |
| | AS | 0.68% | | |
| | YE | 0.6% | | |
| 9. MYP-I | YE | 1% | 100 ml | $1.75 \times 10^8$ |
| | Peptone | 0.2% | | |
| 10. MYP-IV | YE | 0.4% | 100 ml | $1.61 \times 10^8$ |
| | Peptone | 0.4% | | |
| 11. MYP-VI | YE | 0.5% | 100 ml | $2.3 \times 10^8$ |
| | Peptone | 1.5% | | |
| | NaCl | 0.2% | | |
| 12. YPN-VIII | YE | 1.5% | 100 ml | $2.5 \times 10^8$ |
| | Peptone | 0.75% | | |
| | NaCl | 0.2% | | |
| 13. SANYSH | SA | 1% | 100 ml | $1.48 \times 10^8$ |
| | Peptone | 0.5% | | |
| | NaCl | 0.5% | | |
| | BE | 0.5% | | |
| | YE | 0.03% | | |

SA = Sodium Acetate.
YE = Yeast Extract.
BE = Beef Extract.
AS = Ammonium Sulphate All media had trace elements in the following composition: $CaCl_2$-0.013%, $MgCl_2$-0.01%, $MnSO_4$-0.028%, $ZnSO_4$-0.0005%, $FeSO_4$-0.0001%, $CuSO_4$-0.0001%).

pH of the media was 7.2

As will be apparent from the Table 1, the media composition comprises 0.03% to 1.5% of yeast extract, with or without each of 0.2 to 1% of peptone, 1 to 1.6% of sodium acetate, 0.3 to 0.5% of beef extract and 0.5% of sodium chloride was found to be the preferred quantities. The pH of the media was maintained at pH 7.2.

Reference is now made to FIG. 1 of the accompanying drawings which illustrates the flow diagram of the process of preparing the new enzyme. The fermentation broth is subjected to a process of purification consisting of a plurality steps. The first step A is that of micro filtration and wherein the fermented broth is passed through a membrane filter of for example, 0.22μ. The second step of purification consisting in the step of ultra filtration B of the filtrate F1 to remove particles having a molecular weight of more than 1,000,000. The retentate R from such a step is used for activity check and is recycled. The filtrate F2 is subjected to a second step of ultra filtration C to have a retentate R1 with a molecular weight of 10,000 to 1,000,000. The filtrate F3 is rejected.

The retentate R1 is subjected to the step of cell removal by precipitation D with ammonium sulphate having a concentration of up to 40% and preferably 20 to 40%.

The precipitate P1 is then subjected to the step of dialysis E followed by acetone precipitation. The precipitated enzyme is reconstituted in 0.01 to 8.0 M pH and further precipitated G with cold acetone at the ratio of 1:1 to 1:1.5 (v/v). Such a step reduces the volume and contaminants.

The Precipitate P2 is subjected to a step of decolourization H. The precipitate obtained by acetone precipitation was reconstituted in minimum volume of buffer and subjected to decolourization using cell debris remover (CDR), Whatman. Briefly, a bed of CDR is made using a buchner funnel and the crude enzyme was layered over it and vacuum applied to the receiving flask. This is followed by elution with this Tris 0.01 M, pH 8.0 containing 0.1 M NaCl (2-3 bed volumes of buffer) to elute the fibrinolytic enzyme bound to the CDR. This method results in less than 6% activity loss.

Hence the present method describes a process for the increase in the yield of Thrombinase by increasing the yield by this modified CDR treatment as shown in Table 2.

TABLE 2

| TREATMENT | ACTIVITY (IU) | LOSS % |
|---|---|---|
| Before CDR Treatment | 2,36,24,000 | — |
| CDR treatment by reported Method | 3,51,000 | 98% |
| CDR treatment by present Method | 2,21,50,200 | 6% |

The colourless aqueous filtrate F3 is passed through an express ion exchanger I and then subjected to the step J of dialysis against distilled water for removal of the salt followed by the step K of solubilization and lyophilization L. Thus, the CDR treated material was first subjected to ion exchange chromatography. The CDR treated material was first loaded onto the column and eluted first with 0.01 M containing 0.1 M NaCl and subsequently with Tris containing 0.5 M NaCl. The fibrinolytic enzyme eluted with Tris containing 0.1 M NaCl, which was dialysed and lyophilized.

The lyophilized fraction was further purified by the step M of gel filtration chromatography using for example Sephacryl S-200. Elution was carried out using Tris buffer 0.01 M, pH 8.0 containing 0.1 M NaCl. The fraction showing fibrinolytic activity was dialyzed and lyophilized to yield pure Thrombinase.

PRODUCT CHARACTERISATION

The molecular weight of Thrombinase was found to be in the range of 31,000 to 32000, preferably around 31700 as determined by mass spectral analysis. This enzyme is very much different with the enzyme disclosed in the U.S. Pat. No. 5,434,059 having the molecular weight of 18,500 obtained by gel filtration.

The molecular weight of the new enzyme of the present invention has been confirmed by the following experiments.

Amino Acid Composition:

A sample of Thrombinase prepared by the process of the invention was hydrolyzed and subjected to Amino Acid Analyzer (Hitachi L8 500A). It predicted a sample molecular weight in the range of 31,000 to 32000 Daltons as shown in Table 3.

TABLE 3

AMINO ACID ANALYSIS REPORT

| Amino Acid | Nanomoles | Residues (Theory) | Mmol/Res. | MW | Mass (μg) | Mole % | Residue (Found) |
|---|---|---|---|---|---|---|---|
| Aspartic Acid | 13.41 | 33 | 0.41 | 115.1 | 1.54 | 12.52 | 32.35 |
| Threonine | 7.56 | 18 | 0.42 | 101.1 | 0.76 | 7.06 | 18.24 |
| Serine | 10.28 | 25 | 0.41 | 87.1 | 0.90 | 9.60 | 24.80 |
| Glutamic Acid | 6.68 | 16 | 0.42 | 129.1 | 0.86 | 6.34 | 16.12 |
| Proline | 3.59 | 9 | 0.40 | 97.1 | 0.35 | 3.35 | 8.66 |
| Glycine | 12.55 | 31 | 0.41 | 57.1 | 0.73 | 12.00 | 31.00 |
| Alanine | 13.78 | 33 | 0.42 | 71.1 | 0.97 | 12.79 | 33.05 |
| Half-cysteine | | | 0.00 | 103.2 | 0.00 | 0.00 | 0.00 |
| Valine | 6.12 | 15 | 0.41 | 99.1 | 0.41 | 5.71 | 14.77 |
| Methionine | 1.11 | 3 | 0.37 | 131.2 | 0.15 | 1.06 | 2.68 |
| Isoleucine | 7.48 | 18 | 0.42 | 113.2 | 0.85 | 6.98 | 18.05 |
| Leucine | 5.82 | 14 | 0.42 | 113.2 | 0.66 | 3.43 | 14.04 |
| Tyrosine | 5.63 | 14 | 0.40 | 163.2 | 0.92 | 5.24 | 13.58 |
| Phenylalanine | 1.38 | 3 | 0.46 | 147.2 | 0.20 | 1.29 | 3.33 |
| Histidine | 5.10 | 12 | 0.43 | 137.2 | 0.70 | 4.76 | 12.30 |
| Lysine | 2.95 | 7 | 0.42 | 128.2 | 0.38 | 2.75 | 7.12 |
| Arginine | 3.66 | 8 | 0.43 | 156.2 | 0.54 | 3.21 | 8.30 |
| Cysteic Acid | | | 0.00 | 151.2 | 0.00 | 0.00 | 0.00 |
| SCMC | | | 0.00 | 129.1 | 0.00 | 0.00 | 0.00 |
| Met Sufone | | | 0.00 | 167.2 | 0.00 | 0.00 | 0.00 |
| Met Sulfoxide | | | 0.00 | 149.2 | 0.00 | 0.00 | 0.00 |
| Norleucine | | | 0.00 | 113.2 | 0.00 | 0.00 | 0.00 |
| Other | | | 0.00 | | 0.00 | 0.00 | 0.00 |
| | 107.10 | 259 Entries 16 | 0.41 6.63 0.55 | | 11.12 | 100.00 | |

Comments:

1) Special procedures for the quantitation of Cysteine & Trp. were not performed 2) Peptide protein content was very low - ~3%.

Figure 2:
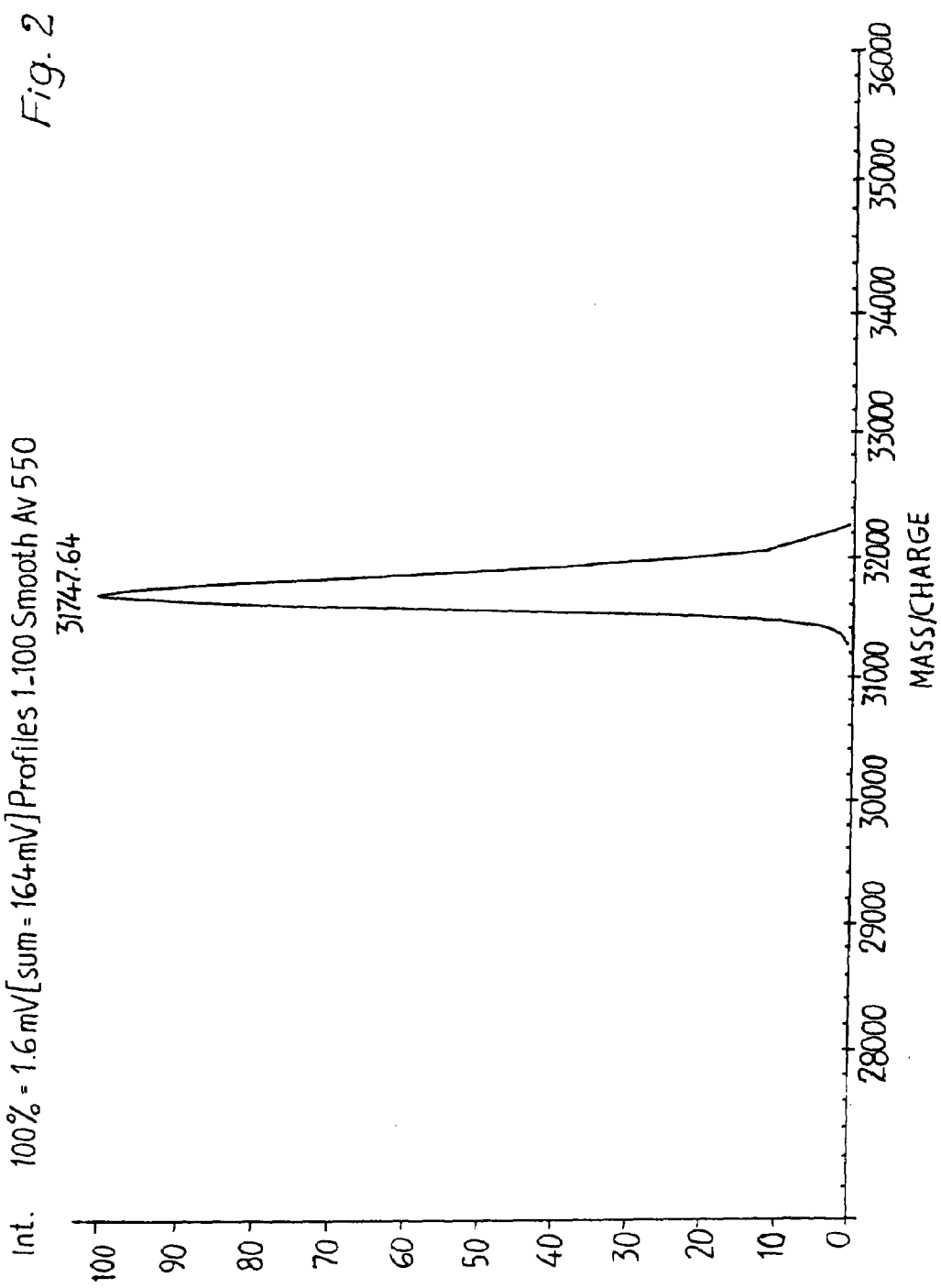
FIG. 2 is a Matrix assisted laser desorption ionization analysis of thrombinase.

Matrix Assisted Laser Desorption Ionization (MALDI):

The average mass of the enzyme prepared by the process of the present invention was analyzed by MALDI TOF (Time of Flight) instrument (Kompact SEQ Spectrometer—Kratos-Shimadzu Analytical, Manchester, UK). It was found that an average mass value of around 31,747 Daltons was obtained by samples from different batches as shown in FIG. 2.

Figure 3:
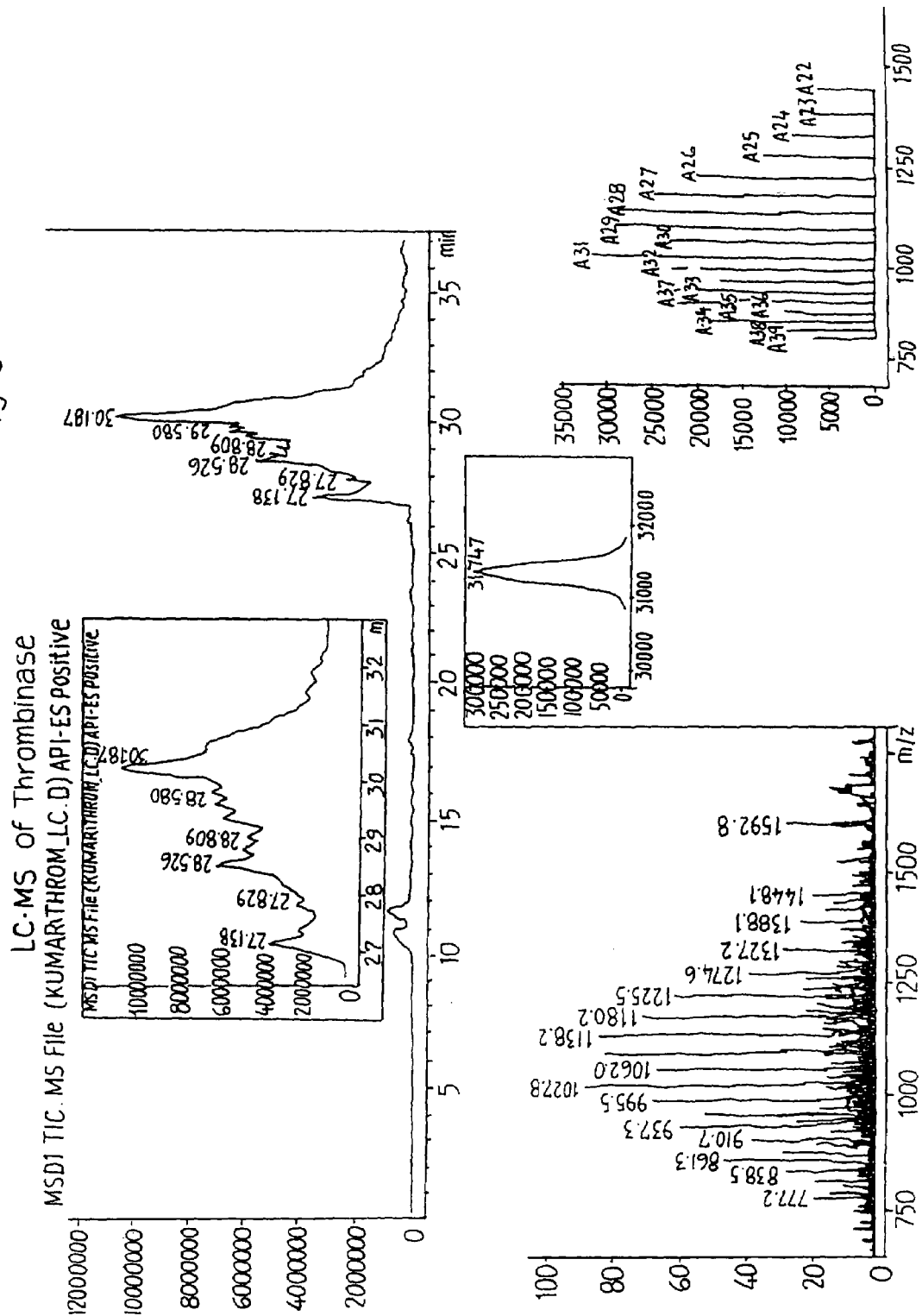
FIG. 3 is a liquid chromatograph mass spectrograph analysis.

Liquid Chromatography Mass Spectrometry:

The mass spectral analysis of the enzyme prepared by the process of the invention was performed in the Electrospray Ionization (ESI) Mass Spectrometry (Hewlett Packard—Model HP-1100). It was observed that that the average mass value was 31,834 Daltons as shown in FIG. 3.

From the above-mentioned results it is predicted that the molecular weight of the new enzyme will be around 31,000 to 32,000 Daltons.

Figure 4:
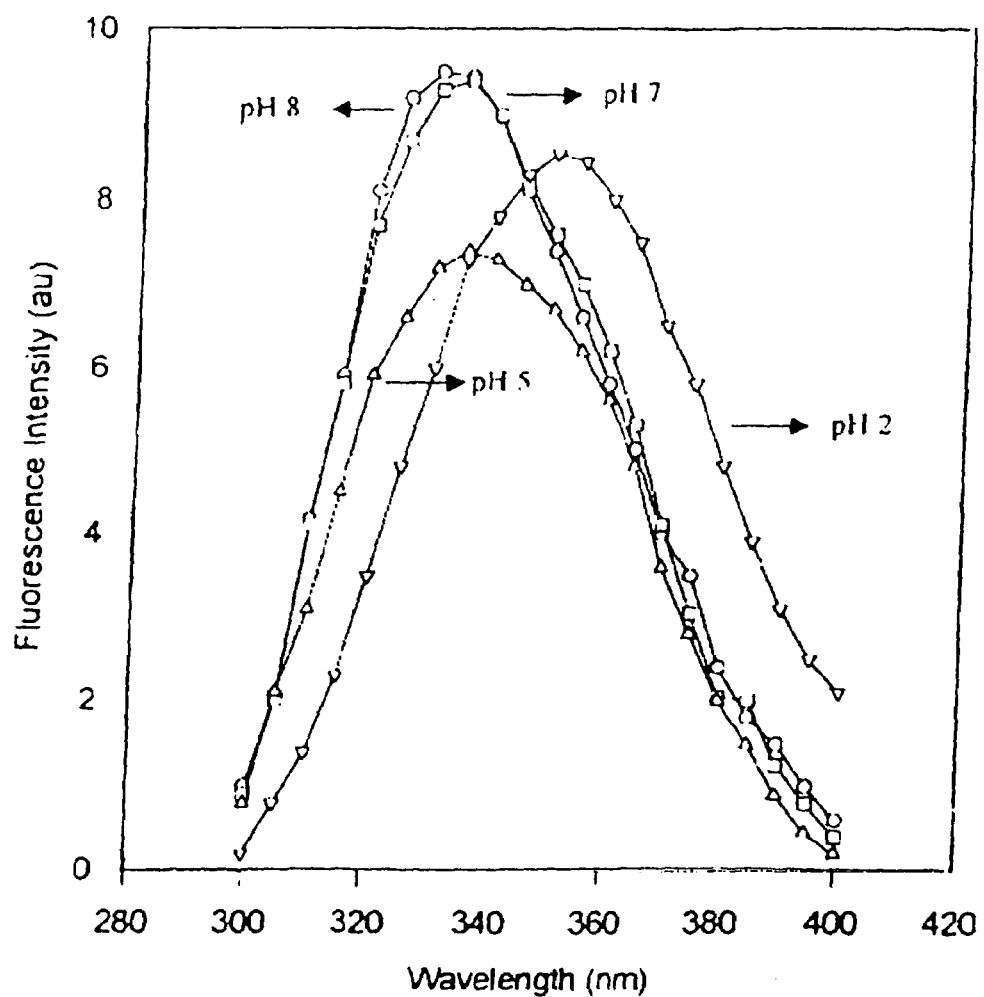
FIG. 4 is a fluorescence analysis of Thrombinase.

Fluorescence Spectrum:

Fluorescence analysis of Thrombinase by Hitachi 650-60 Spectrofluorimeter for fluorescence showed that the molecule is partially unfolded at pH 5.0 and completely unfolded at pH 2.0. The observation gives the explanation for the reduction in activity of Thrombinase at pH 5.0 and reversion to the normal activity at pH 8.0 (from unfolded to folded form) FIG. 4.

Figure 5:
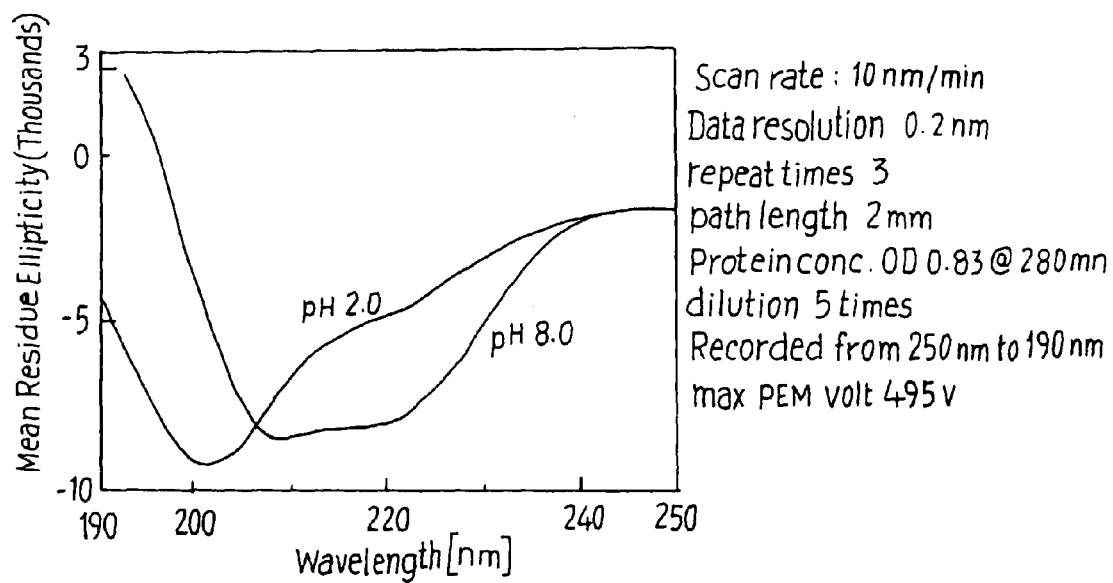
FIG. 5 is a far UV analysis of Thrombinase.
Figure 6:
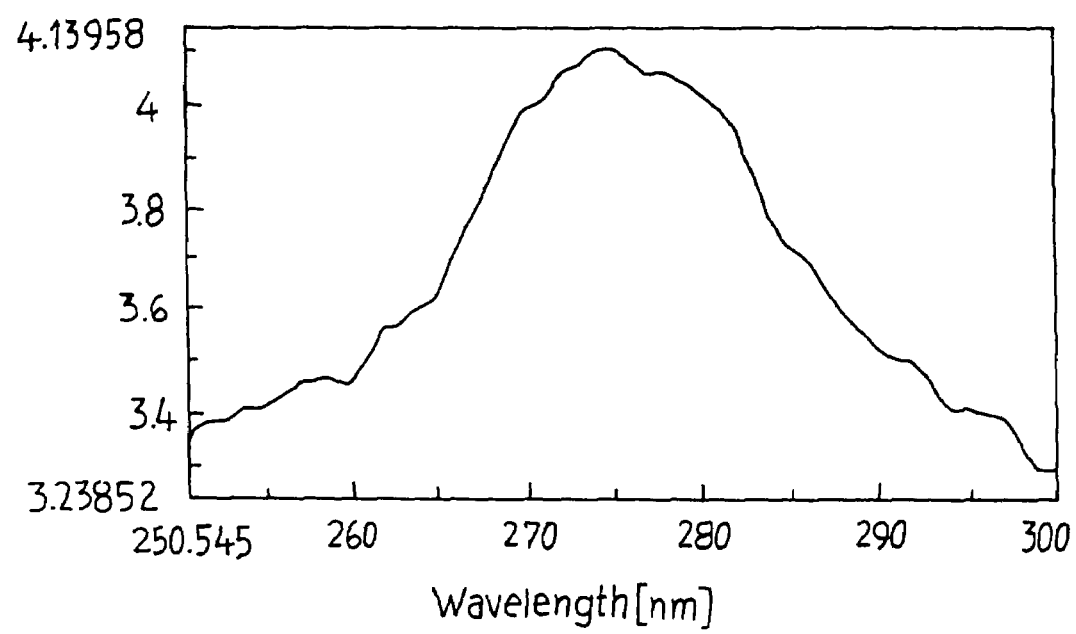
FIG. 6 is a near UV CD analysis of Thrombinase

Circular Dichorism:

The Circular Dichorism (CD) studies were conducted for Thrombinase in JASCO J-715 Spectropolarimeter. The far UV CD analysis showed that the molecule possesses alpha ($\alpha$) helices and Beta ($\beta$) sheets in the secondary structure (FIG. 5) and the near UV CD analysis showed absence of tertiary structure (FIG. 6).

The effect of Thrombinase on the osmotic fragility of human RBCs have been determined by incubating the RBCs at 100 and 1000 times the therapeutic level (30000 and 300000 IU per milliliter of blood) for 30 minutes followed by evaluation of osmotic fragility of the RBCs at varying concentrations of sodium chloride (0%-0.85%). Such tests indicate no changes in the osmotic fragility pattern over the entire range of sodium chloride and hence indicating that Thrombinase does not affect the RBCs.

The tests on the effect of Thrombinase on different protein substrates like casein, fibrinogen and bovine serum albumin shows that Thrombinase acts preferentially on fibrin with very little activity on other protein substrates.

TABLE 3

| SUBSTRATE | ACTIVITY (IU) |
|---|---|
| Casein | 1431 |
| Fibrinogen | 634 |
| Bovine Serum Albumin | 919 |
| Fibrin Clot | 170,000 |

The invention claimed is:

1. A biologically purified and isolated thrombinase having a molecular weight in the range of 31,000 to 32,000 Daltons useful in dissolving blood clots for medical conditions.

2. The thrombinase of claim 1, wherein the thrombinase has a molecular weight of 31,700 Daltons useful in dissolving blood clots.

3. The thrombinase of claim 1, wherein the thrombinase is prepared by: (i) Culturing of cells of *Bacillus sphaericus* serotype H5a 5b in a culture medium consisting of 0.03 to 1.5% of yeast extract, 0.2 to 1.5% peptone, 1 to 1.6% sodium acetate, 0.3 to 0.5% beef extract, 0.2 to 0.5% sodium chloride, 0.5 to 1% Soya peptone, and 0.68% ammonium sulphate at a pH in a range of 7.2 to 8, (ii) Removing the cultured cells by cross flow filtration using 0.22 mµ filter to obtain a cell supernatant, (iii) Subjecting the cell supernatant to two step ultra filtration: a. with a first ultra filtration of the cell supernatant using 100,000 MW (Molecular Weight) cut off membrane to obtain a filtrate, and b. with a second ultra filtration of the filtrate using 10,000 MW cut off membrane to obtain a retentate, (iv) Salting out the retentate with ammonium sulphate in a concentration in the range of 20 to 40% to obtain a precipitate, (v) Subjecting the precipitate to dialysis, (vi) Re-precipitating the dialyzed precipitate using ice-cold acetone to obtain a re-precipitated precipitate, (vii) Reconstituting the re-precipitated precipitate in buffer, (viii) Decolorizing the reconstituted precipitate, and then dialyzing and lyophilizing to obtain a lyophilized precipitate, (ix) Subjecting the lyophilized precipitate to ion exchange chromatography and to gel filtration chromatography to obtain a fraction showing fibrinolytic activity, and (x) Dialyzing the fraction showing fibrinolytic activity and lyophilizing to obtain the purified thrombinase.

4. The thrombinase of claim 3, wherein the buffer used in step (vii) is Tris 0.01 M and the pH is 8.0.

5. The thrombinase of claim 3, wherein the amount of ice-cold acetone and re-precipitated precipitate in step (vi) are in the ratio of 1:1 to 1:1.5 (v/v).

6. The thrombinase of claim 3, wherein the amount of ice-cold acetone and re-precipitated precipitate in step (vi) are in the ratio of 1:1 to 1:1.5 (v/v).

7. The thrombinase of claim 1, wherein the medical condition comprises myocardial infarction or pulmonary thrombosis which arises due to occlusion of arteries or veins.

8. The thrombinase of claim 1, wherein the thrombinase is prepared by culturing *Bacillus sphaericus* sero type H5a 5b, removing the cells, subjecting a cell supernatant to filtration, salting out a retenatate, subjecting a precipitate from the salting out to dialysis, reprecipitating the precipitate and then reconstituting the precipitate in buffer and finally decolorizing, purifying and dialyzing the precipitate.

9. A method of treating cerebral thrombosis, myocardial infraction and deep vein thrombosis comprising administering thrombinase having a molecular weight in the range of 31,000 to 32,000 to a patient in need thereof and thereby dissolving in vivo a blood clot of said patient.

10. The method of claim 9, wherein the thrombinase is administered to the patient via injection or parenterally.

11. The method of claim 9, wherein the thrombinase is prepared by culturing *Bacillus sphaericus* sero type H5a 5b, removing the cells, subjecting a cell supernatant to filtration, salting out a retenatate, subjecting a precipitate from the salting out to dialysis, reprecipitating the precipitate and then reconstituting the precipitate in buffer and finally decolorizing, purifying and dialyzing the precipitate.

12. The method of claim 9, wherein the thrombinase is prepared by: (i) Culturing cells of Bacillus sphaericus serotype H5a 5b in a culture medium consisting of 0.03 to 1.5% of yeast extract, 0.2 to 1.5% peptone, 1 to 1.6% sodium acetate, 0.3 to 0.5% beef extract, 0.2 to 0.5% sodium chloride, 0.5 to 1% Soya peptone, and 0.68% ammonium sulphate at a pH in a range of 7.2 to 8, (ii) Removing the cultured cells by cross flow filtration using 0.22 mµ filter to obtain a cell supernatant, (iii) Subjecting the cell supernatant to two step ultra filtration: a. with a first ultra filtration of the cell supernatant using 100,000 MW (Molecular Weight) cut off membrane to obtain a filtrate, and b. with a second ultra filtration of the filtrate using 10,000 MW cut off membrane to obtain a retentate, (iv) Salting out the retentate with ammonium sulphate in a concentration in the range of 20 to 40% to obtain a precipitate, (v) Subjecting the precipitate to dialysis, (vi) Re-precipitating the dialyzed precipitate using ice-cold acetone to obtain a re-precipitated precipitate, (vii) Reconstituting the re-precipitated precipitate in buffer, (viii) Decolorizing the reconstituted precipitate, and then dialyzing and lyophilizing to obtain a lyophilized precipitate, (ix) Subjecting the lyophilized precipitate to ion exchange chromatography and to gel filtration chromatography to obtain a fraction showing fibrinolytic activity, and (x) Dialyzing the fraction showing fibrinolytic activity and lyophilizing to obtain the purified and isolated thrombinase.

\* \* \* \* \*